United States Patent [19]

Wade

[11] Patent Number: 4,476,130
[45] Date of Patent: Oct. 9, 1984

[54] 3-(1H-TETRAZOL-5-yl)-4H-PYRIMIDO[2,1-b]BENZOXAZOL-4-ONE COMPOUNDS EXHIBITING ANTI-ALLERGIC ACTIVITY

[75] Inventor: James J. Wade, Oakdale, Minn.

[73] Assignee: Riker Laboratories, Inc., St. Paul, Minn.

[21] Appl. No.: 416,243

[22] Filed: Sep. 9, 1982

[51] Int. Cl.³ ................... A61K 31/505; C07D 498/04
[52] U.S. Cl. ..................................... 424/251; 544/250; 548/222
[58] Field of Search ......................... 544/250; 424/251

[56] References Cited

U.S. PATENT DOCUMENTS 3,538,086 11/1970 Mair et al. ...................... 544/250 X
3,585,198 6/1971 Meszaros et al. ................... 260/251
4,122,274 10/1978 Juby ................................... 544/282
4,209,620 6/1980 Juby ................................... 544/252
4,223,031 9/1980 Covington et al. ................ 424/251

OTHER PUBLICATIONS

Derwint Abstract for Japanese Application 58177991
Sam and Plampin, *J. Pharm. Sci.*, 53, 538–544, (1964).
Yevich et al., *J. Med. Chem.*, 25, 864–868, published Jul. 1982.

*Primary Examiner*—Donald G. Daus
*Assistant Examiner*—Diana G. Rivers
*Attorney, Agent, or Firm*—Donald M. Sell; James A. Smith; Robert W. Sprague

[57] ABSTRACT 3-(1H-tetrazole-5-yl)-4H-pyrimido[2,1-b]-benzoxazol-4-ones are disclosed as anti-allergic compounds. Pharmaceutically acceptable salts, pharmaceutical compositions containing the compounds and methods of using the compounds are also disclosed.

8 Claims, No Drawings

3-(1H-TETRAZOL-5-yl)-4H-PYRIMIDO[2,1-b]BENZOXAZOL-4-ONE COMPOUNDS EXHIBITING ANTI-ALLERGIC ACTIVITY

FIELD OF THE INVENTION

This invention relates to novel 3-(1H-tetrazol-5-yl)-4H-pyrimido[2,1-b]benzoxazol-4-one compounds which exhibit anti-allergic activity. This invention also relates to a pharmaceutical composition containing the compounds, and a method of using the compounds.

BACKGROUND OF THE INVENTION

U.S. Pat. Nos. 4,122,274 and 4,209,620 describe 3-(1H-tetrazol-5-yl)-4H-pyrido[1,2-a-]pyrimidin-4-ones and the antiallergy activity exhibited by such compounds. U.S. Pat. No. 4,223,031 describes 3-(1H-tetrazol-5-yl)-4H-pyrimido[2,1-b]benzothiazol-4-ones and 6-(1H-tetrazol-5-yl)thiazolo[3,2-a]pyrimidin-5-ones and the antiallergy activity exhibited by such compounds. Sam and Plampin, *J. Pharm. Sci.*, 53, 538 (1964) describes substituted 2-aminobenzoxazoles and substituted benzoxazolinones which are skeletal muscle relaxants.

DETAILED DESCRIPTION

The present invention relates to novel compounds of the formula I

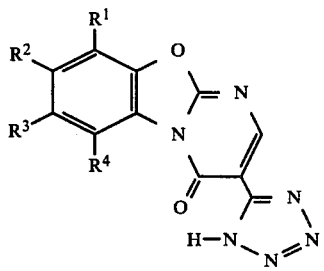

wherein $R^1$, $R^2$, $R^3$ and $R^4$ are each independently selected from the group consisting of hydrogen, an alkyl group containing 1 to about 4 carbon atoms, an alkoxy group containing 1 to about 4 carbon atoms and halogen. Chlorine is the preferred halogen substituent. Compounds of formula I form salts with organic amines, ammonia, alkali metal hydroxides, alkali metal carbonates, alkali metal bicarbonates, metal hydrides and alkali metal hydroxides, and all such salts are within the scope of the invention. The compounds of the invention exhibit antiallergic activity.

A further aspect of the invention relates to a method for inhibiting the effects of an antigen-antibody reaction in mammals, including humans, comprising delivering to the known or expected area of the mammalian body where said reaction has occurred or is expected to occur an effective amount of a compound of Formula I or a pharmaceutically acceptable salt thereof. Preferably, the method is practiced prior to the antigen-antibody reaction.

A two-step process for the preparation of compounds of Formula I is illustrated in general terms in Procedure A below:

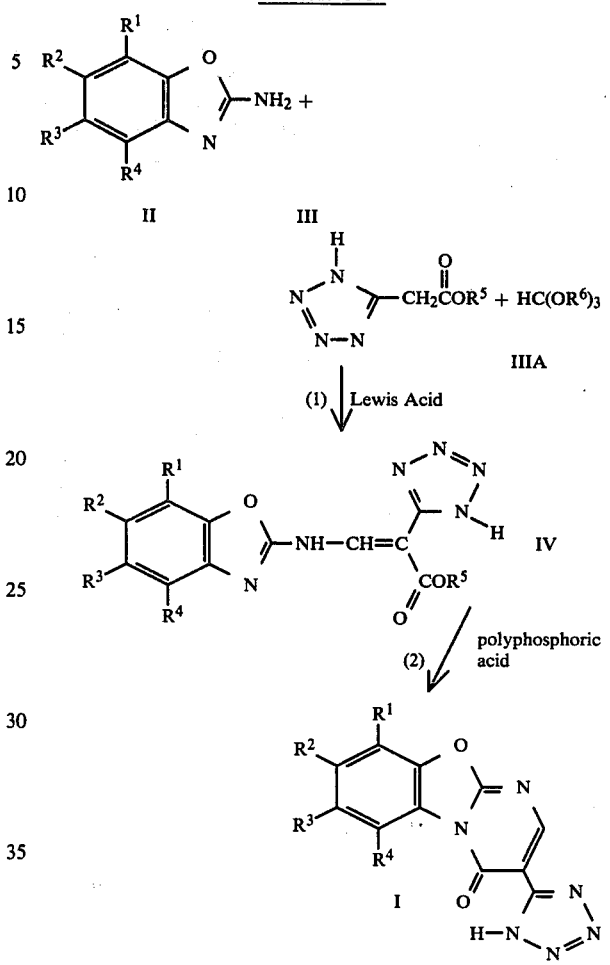

wherein $R^1$, $R^2$, $R^3$ and $R^4$ are as defined previously; $R^5$ is an alkyl group containing 1 to about 4 carbon atoms; and each $R^6$ is independently an alkyl group containing 1 to about 4 carbon atoms.

In step (1) of Procedure A, a 2-aminobenzoxazole of Formula II, an alkyl tetrazol-5-ylacetate of Formula III and a trialkyl orthoformate ester of Formula IIIA are reacted together in the presence of a Lewis acid catalyst. The product is the novel intermediate of Formula IV.

Suitable 2-aminobenzoxazoles which may be employed in step (1) are well known in the art and include 2-aminobenzoxazole, 2-amino-5-chlorobenzoxazole, 2-amino-5-methoxybenzoxazole, 2-amino-6-chlorobenzoxazole, 2-amino-5-methylbenzoxazole, 2-amino-7-chlorobenzoxazole, 2-amino-6-bromo-5-chlorobenzoxazole, 2-amino-5,6-dichlorobenzoxazole and 2-amino-4-chlorobenzoxazole.

Ethyl tetrazol-5-ylacetate is the preferred alkyl tetrazol-5-ylacetate of Formula III. The mole ratio of alkyl tetrazol-5-ylacetate of Formula III to the 2-amino-benzoxazole of Formula II is preferably about 1:1.

Examples of suitable trialkyl orthoformate esters IIIA for employment in step (1) are trimethyl orthoformate and triethyl orthoformate. One mole of trialkyl orthoformate per mole of alkyl tetrazol-5-ylacetate of Formula III is required to obtain complete reaction. It is preferred that a slight molar excess of the trialkyl orthoformate ester be employed.

Examples of suitable Lewis acid catalysts for employment in step (1) are zinc chloride and stannous chloride. The preferred catalyst is aluminum trichloride. Weaker acids such as boron trifluoride and p-toluenesulfonic acid generally provide poorer yields in most cases and are not preferred. Catalytic amounts, e.g., less than 30 mole percent and preferably about 10 mole percent of catalyst, are used.

The reaction of step (1) may be conducted by combining the reactants and heating at about 100° to 150° C. Any volatile distillates may be collected if such is desired. The reaction of step (1) may be carried out in an inert solvent such as dioxane or trichloroethylene. The intermediate of Formula IV may be isolated at this point and be further purified or the reaction product of step (1) may be used directly in step (2) without isolation of the intermediate of Formula IV.

In step (2) the intermediate of Formula IV is preferably combined with polyphosphoric acid and heated to effect cyclization to the desired product of Formula I. The mixture is generally heated in the absence of solvent at 100° to 150° C.

An alternative, one-step procedure for the preparation of the compounds of Formula I is illustrated in general terms in Procedure B below:

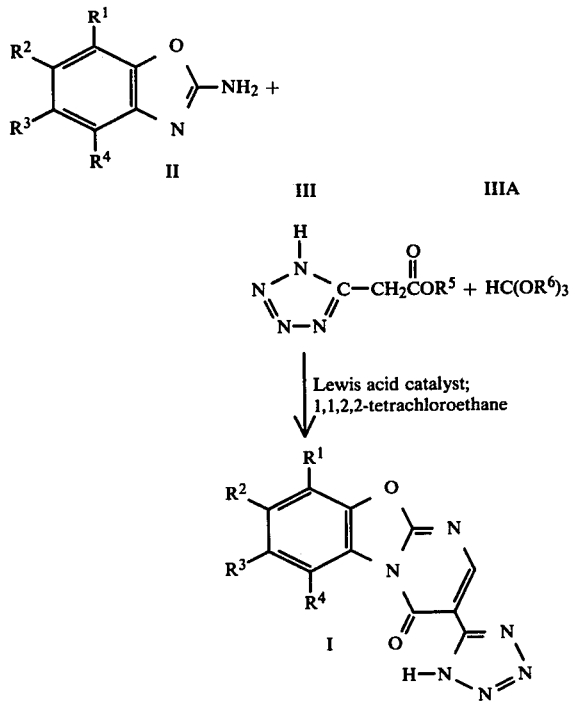

Procedure B wherein $R^1$, $R^2$, $R^3$, $R^4$, $R^5$ and $R^6$ are as defined previously.

In Procedure B, reaction of a 2-aminobenzoxazole of formula II, an alkyl tetrazol-5-ylacetate of Formula III and a trialkyl orthoformate of Formula IIIA in the presence of a Lewis acid catalyst and the cyclization of the resulting intermediate to form the compound of Formula I occur sequentially in a one-step process when the indicated 1,1,2,2-tetrachloroethane is employed as the solvent. The reaction mixture is generally heated at about 100° to 150° C., 130° C. being the preferred temperature. Suitable trialkyl orthoformate esters and Lewis acid catalysts include those discussed above in connection with Procedure A.

The final product of either Procedure A or B is readily isolated and purified using conventional methods such as extraction, filtration, recrystallization and chromatography.

The compounds of the invention have been shown to inhibit the release and/or synthesis and/or effect of biochemical products which produce an allergic reaction through an antibody-antigen reaction. Both subjective and objective changes which result from the inhalation of specific antigens by sensitized subjects may be markedly inhibited by administration of the compounds of the invention.

The compounds are useful in the treatment of so-called "intrinsic" asthma (in which no sensitivity to extrinsic antigen can be demonstrated) or any condition in which non-specific factors trigger the release of allergic mediators. The compounds of the invention are also useful in the treatment of other conditions in which antigen-antibody reactions are responsible for disease such as extrinsic asthma, food allergies, allergic rhinitis, allergic conjunctivitis, atopic dermatitis, hay fever, urticaria and auto-immune diseases.

A further embodiment of the invention therefore is a pharmaceutical composition comprising a compound of formula (I) formulated with a pharmaceutically acceptable carrier or diluent.

The nature of the pharmaceutical composition and the carrier or diluent will, of course, depend upon the desired mode of administration. Suitable modes of administration of the compounds of the invention include oral administration, administration by inhalation (including both oral and nasal inhalation), subcutaneous administration, intravenous administration, parenteral administration and topical administration. Suitable pharmaceutical compositions comprising a compound of the invention may be formulated in the conventional manner with conventional ingredients, e.g., the pharmaceutical compositions may be solutions, suspensions, syrups, dry powders, tablets or, when intended for topical application, creams, lotions or pastes. The pharmaceutical compositions of the invention generally comprises a minor proportion of the compound of the invention and a major proportion of a carrier or diluent.

The pharmaceutical compositions are preferably administered by inhalation, particularly when treating allergic asthma. For this mode of administration, the compounds of the invention are dissolved or suspended in water either as the free acid or as a salt such as the sodium salt. The resulting solution or suspension may be applied by means of a conventional nebulizer. Alternatively, a pressurized dispensing container (e.g., an aerosol dispenser) may be used. Aqueous solutions or suspensions which are to be administered by means of a conventional nebulizer may contain up to about 10 percent by weight of the compound of the invention. Pharmaceutical compositions which are to be dispensed from a pressurized container comprising suspensions or solutions in liquified propellants normally contain about 0.2 to 5 percent by weight of the active compound.

For administration from an aerosol dispenser, a compound of the invention is dissolved or suspended in a liquified propellant medium. Suitable propellants are those conventionally used in formulations which are dispensed from pressurized containers. For example, halogenated hydrocarbons such as those described in U.S. Pat. No. 2,868,691 may be used. Preferred propellants are difluorodichloromethane, dichlorotetrafluoroethane and mixtures thereof. When the compound of the invention is insoluble in the propellant, it may be necessary to employ a surface-active agent in order to provide a suitable suspension of the compound in the propellant medium. Suitable surface-active agents are known to those skilled in the art and include nonionic surface-active agents. The use of such surface-active agents and the advantages which result therefrom are more fully described in British Patent Specification No. 1,063,512.

When formulated as powders, the pharmaceutical compositions of the invention may be administered by means of a conventional insufflator device. In order to obtain powders which may be suitably administered by such a method, it may be desirable to modify the surface characteristics of the powder particles, for example, by coating them with a pharmaceutically acceptable material such as sodium stearate. In addition, it may be desirable to mix a coarser diluent material, such as lactose, with a finely divided powder of the compound of the invention. The amount of the diluent material present in such compositions will vary depending on the results desired. For example, such mixtures may contain from 50 to 150 percent by weight of the diluent material based on the total weight of the compound of the invention and such other active ingredients as may be present.

The compounds of the invention may also be administered using dispensers from which metered amounts of the compound are discharged for administration by oral or nasal inhalation. The propellant in such dispensers may be compressed air or other compressed inert gases such as nitrogen, argon and the like.

The compounds of the invention may also fine use in the treatment of allergic eye conditions. For example, the compounds may be useful in treating the condition associated with hay fever, i.e., allergic conjunctivitis. For such use, the compounds may be used as eye drops and/or sprays in the form of an isotonic aqueous solution containing about two percent of the compound and an effective amount of a preservative.

As noted previously, the compounds of the invention are indicated for use in inhibiting the effects of antibody-antigen reactions. The treatment may be one which requires repeated dosages of the compound at regular intervals. The amount of compound and frequency of administration will depend upon many factors, and no concise dosage rate or regimen can be generally stated. However, as a general guide, where the compounds of the invention are administered by inhalation to a patient suffering from acute allergic asthma, thereapeutically useful results may be achieved when doses of 0.1 to 20 mg/kg per dose are used. When the compounds are administered by oral routes, dosages such as 1 to 100 mg are normally given.

Other active ingredients may also be present in the pharmaceutical compositions of the invention. Thus, in compositions which are to be administered by inhalation, it may be beneficial to include a bronchodilator such as isoprenaline, adrenaline, carbuterol, rimiterol, orciprenaline, isoetharine or derivatives (e.g., salts) of the foregoing. The amount of bronchodilator used will vary depending upon the nature and activity of the bronchodilator and the compound of the present invention which is employed. Generally, the use of a minor proportion (i.e., less than 50 percent by weight) of the bronchodilator together with from 0.1 to 10 percent by weight of the compound of the present invention is preferred.

The following examples are provided for the purpose of further illustrating the invention but are not intended to limit the scope thereof in any way.

EXAMPLE 1

Synthesis of
3-(1H-tetrazol-5-yl)-4H-(pyrimido[2,1-b]benzoxazol-4-one

A mixture of 6.70 g (50.0 mmole) of 2-aminobenzoxazole, 7.8 g (50.0 mmole) of ethyl tetrazol-5-ylacetate and 10.0 g (67.8 mmole) of triethyl orthoformate was heated to 120° C., followed by the addition of 0.3 of aluminum trichloride. The resulting mixture was maintained at 120° C. for about 40 minutes and subsequently cooled and triturated with 20 ml of methanol. The mixture was diluted to 100 ml with ice water. The resulting pale yellow solid was separated by filtration, washed with water and methanol, and dried to provide 10.99 g (73%) of ethyl 2-[N-(2-benzoxazolyl)amino]-1-(1H-tetrazol-5-yl)acrylate. Infrared and nuclear magnetic resonance spectral analyses were consistent with the structural assignment.

A stirred mixture of 20 g of polyphosphoric acid and 1.00 g (3.33 mmole) of the ethyl 2-[N-(2-benzoxazolyl)amino]-1-(1H-tetrazol-5-yl)acrylate prepared above was heated gradually until foaming began at about 150° C. Heating (at 150° C.) and stirring were continued for 25 minutes at which time the hot mixture was poured into 200 ml of an ice-water mixture. The solid was separated by filtration, washed thoroughly with water, and extracted twice with 100 ml of hot water. The product was 0.44 g (52%) of pale yellow-colored solid. The solid was further purified in combination with the product from another run on a 5.00 mmole scale by combining the solids and recrystallizing from a mixture of N,N-dimethylformamide and water (20 ml/5 ml, respectively). The recrystallized product was washed twice with 50 ml portions of hot water to provide white-colored solid 3-(1H-tetrazol-5-yl)-4H-pyrimido[2,1-b]benzoxazol-4-one. Analysis: Calculated for $C_{11}H_6N_6O_2$: %C, 52.0; %H, 2.4; %N, 33.1; Found: %C, 52.0; %H, 2.2; %N, 33.1. The structural assignment was confirmed by infrared and nuclear magnetic resonance spectral analyses.

EXAMPLE 2

Alternative Synthesis of
3-(1H-Tetrazol-5-yl)-4H-pyrimido[2,1-b]benzoxazol-4-one A mixture of 1.34 g (10.0 mmole) of 2-aminobenzoxazole, 1.56 g (10.0 mmole) of ethyl tetrazol-5-ylacetate, 1.65 g (11.1 mmole) of triethyl orthoformate and 0.3 g (2.2 mmole) of aluminum trichloride in 25 ml of 1,1,2,2-tetrachloroethane was heated under a nitrogen atmosphere at 125° to 130° C. for about 19 hours. The mixture was cooled and the resulting solid was separated by filtration and washed with methanol to provide 0.72 g (28%) of crude 3-(1H-tetrazol-5-yl)-4-H-pyrimido[2,1-b]benzoxazol-4-one. Infrared spectral analysis of the crude product confirmed the structural assignment.

EXAMPLE 3

The effectiveness of 3-(1H-tetrazol-5-yl)-4H-pyrimido[2,1-b]benzoxazol-4-one in inhibiting passive cutaneous anaphylaxis in rats was demonstrated using the following standard test method.

Sprague-Dawley rats (male or female) having a body weight of about 200 g. were injected intramuscularly with egg albumin and intraperitoneally with Bordetella pertussis vaccine. Ten to twelve days after this treatment the rats were exsanguinated via the abdominal aorta. The blood was allowed to clot overnight and then centrifuged in order to collect the blood serum which contained the antibody.

Another group of Sprague-Dawley rats in the body weight range of 50 to 120 g. was then sensitized to egg albumin by intradermal injection of 0.1 ml. of the above antibody-containing blood serum into the mid-dorsal region. Sensitivity was allowed to develop for 24 hours. The test compound was then administered to the sensitized rats either by intraperitoneal injection or orally at predetermined time intervals immediately before challenge by intravenous administration of egg albumin and Evans Blue dye. A saline solution containing methyl cellulose (that commercially available under the trade designation ("Klucel" from Hercules) was employed as the vehicle. For each dose level of the compound, a group of six rats were treated, and six rats remained untreated as controls for each test. The dosages of the compound were selected so as to give a range of inhibition values.

After treatment with the test compound, the rats were challenged by intravenous injection of 1 ml. of a mixture of egg albumin (0.5 mg/ml), Evans Blue dye solution (10 mg/ml) and physiological saline. The challenge dose produced an anaphylactic reaction at the site of injection which was rendered visible by the blue dye.

Forty-five minutes after injection of egg albumin the rats were sacrificed and the skins removed and reversed. The intensity of the anaphylactic reaction was assessed by comparing the size (i.e., area determined by multiplying two diameters taken at right angles) of the characteristic blue weal produced by spread of the Evans Blue dye from the sensitization site. Comparison of the size of the weals in the control animals with that of the weals in the treated animals allowed calculation of the results in terms of percent inhibition, i.e.

$$\frac{(\text{Control group area} - \text{treated group area})}{\text{Control group area}} \times 100.$$

In this test, the compound 3-(1H-tetrazol-5-yl)-4H-pyrimido[2,1-b]benzoxazole, when administered intraperitoneally at a dose of 5 mg/kg 24 hours prior to antigenic challenge, resulted in a 98% inhibition of the anaphylactic reaction. The same compound, when administered orally at a dose of 10 mg/kg 24 hours prior to antigenic challenge, resulted in a 59% inhibition of the anaphylactic reaction.

EXAMPLES 4–11

The following Table (I) illustrates several additional compounds of the invention and the known starting materials from which they may be prepared. The procedures which may be employed for obtaining the compounds are those described hereinabove (i.e., either Procedure A or Procedure B).

TABLE I

| Example Number | Known Starting Material | Final Product |
|---|---|---|
| 4 | 2-amino-5-chlorobenzoxazole 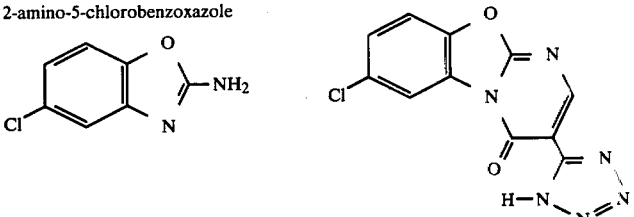 | 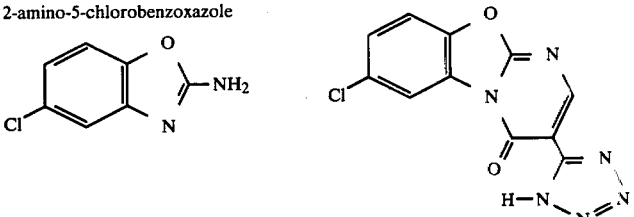 |
| 5 | 2-amino-5-methoxybenzoxazole 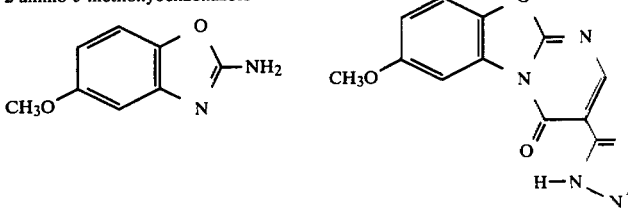 | 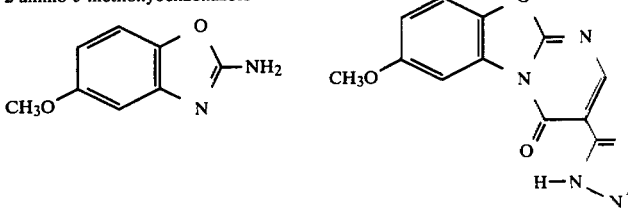 |
| 6 | 2-amino-6-chlorobenzoxazole 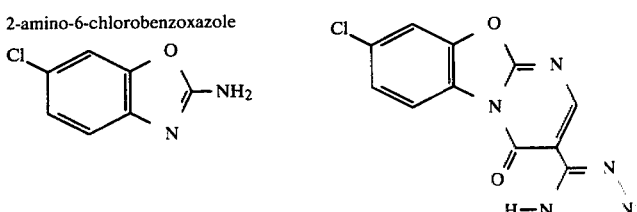 | 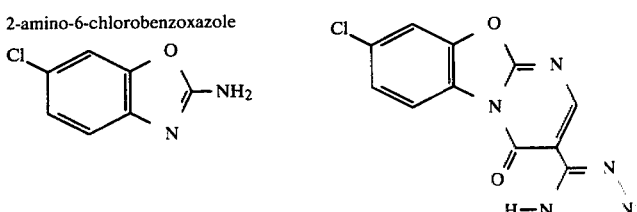 |

TABLE I-continued
| Example Number | Known Starting Material | Final Product |
|---|---|---|
| 7 | 2-amino-5-methylbenzoxazole | |
| 8 | 2-amino-7-chlorobenzoxazole | |
| 9 | 2-amino-4-chlorobenzoxazole | |
| 10 | 2-amino-6-bromo-5-chlorobenzoxazole | |
| 11 | 2-amino-5,6-dichlorobenzoxazole | |
What is claimed is:
1. A compound of the formula
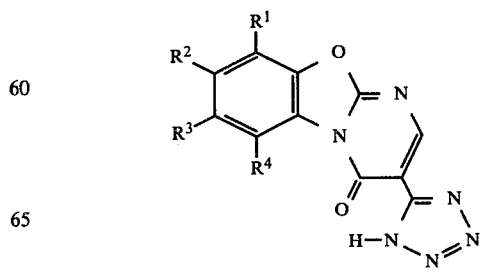

wherein $R^1$, $R^2$, $R^3$ and $R^4$ are each independently selected from the group consisting of hydrogen, an alkyl group containing 1 to about 4 carbon atoms, an alkoxy group containing 1 to about 4 carbon atoms and halogen; and pharmaceutically acceptable salts thereof.

2. The compound 3-(1H-tetrazol-5-yl)-4H-pyrimido[2,1-b]benzoxazole in accordance with claim 1.

3. A pharmaceutical composition for inhibiting allergic reactions in mammals comprising an effective amount of compound of claim 1 and a pharmaceutically-acceptable vehicle.

4. A method for inhibiting antigen-antibody reaction in mammals comprising delivering to the known or expected area of said mammalian body where said reaction has occurred or is expected to occur, an effective amount of a compound according to claim 1.

5. The method according to claim 4, wherein said compound is administered orally to said mammal.

6. The method according to claim 5, wherein the compound is 3-(1H-tetrazol-5-yl)-4H-pyrimido[2,1-b]benzoxazole.

7. The method according to claim 4, wherein said compound is administered to said mammal by inhalation.

8. The method according to claim 4, wherein said compound is administered to said mammal subcutaneously.

* * * * *